(12) United States Patent
Hansen et al.

(10) Patent No.: US 7,976,522 B2
(45) Date of Patent: Jul. 12, 2011

(54) APPLIANCE FOR IRRIGATION AND/OR DRAINAGE

(75) Inventors: Michael Hansen, Gilleleje (DK); Bent Hall Jensen, Charlottenlund (DK)

(73) Assignee: Coloplast A/S, Humlebaek (DK)

( * ) Notice: Subject to any disclaimer, the term of this patent is extended or adjusted under 35 U.S.C. 154(b) by 612 days.

(21) Appl. No.: 11/920,739

(22) PCT Filed: May 19, 2006

(86) PCT No.: PCT/DK2006/000274
§ 371 (c)(1),
(2), (4) Date: Nov. 20, 2007

(87) PCT Pub. No.: WO2006/122562
PCT Pub. Date: Nov. 23, 2006

(65) Prior Publication Data
US 2010/0137821 A1    Jun. 3, 2010

(30) Foreign Application Priority Data

May 20, 2005   (DK) .................................. 2005 00736

(51) Int. Cl.
*A61F 5/44* (2006.01)
(52) U.S. Cl. ........ 604/338; 604/337; 604/339; 604/340; 604/332; 604/333; 604/334; 604/335; 604/336; 604/341; 604/342; 604/343; 604/344; 604/345; 604/346; 604/355; 604/277; 604/278; 600/30; 600/31; 600/32; 128/887
(58) Field of Classification Search .......... 604/332–346, 604/355, 277–278; 600/30–32; 128/887
See application file for complete search history.

(56) References Cited

U.S. PATENT DOCUMENTS

| 2,563,597 A | * | 8/1951 | Friedman | ...................... 604/339 |
| 2,662,525 A | * | 12/1953 | Priebe | ........................... 604/343 |
| 2,667,167 A | * | 1/1954 | Raiche | ........................... 604/339 |

(Continued)

FOREIGN PATENT DOCUMENTS

DE          3637355 A1 *  5/1988

(Continued)

OTHER PUBLICATIONS

WO2004/015657A3 ISR Search Report, Pedersen et al, Dec. 2004.*

(Continued)

*Primary Examiner* — Melanie J Hand
*Assistant Examiner* — Ginger T Chapman
(74) *Attorney, Agent, or Firm* — Coloplast Corp., Coloplast A/S; Daniel G. Chapik; Nicholas R. Baumann (57) ABSTRACT

The invention relates to an appliance for irrigation and/or drainage, which appliance comprising a body side member comprising an adhesive wafer for securing the appliance to the patient's skin, said wafer can be provided with an aperture for receiving a stoma, surrounding a wound, a fistula or a drainage site, a wall of flexible material, the wall comprising a rear wall and a front wall, the rear wall being attached to the wafer and having an opening suitable for surrounding the surface area of the skin to be cleansed, and the front wall comprising a coupling flange adapted for removable coupling and sealing to matching coupling means, an sealed chamber which, when inflated, provides a distance between the adhesive wafer and the coupling flange.

18 Claims, 7 Drawing Sheets

U.S. PATENT DOCUMENTS

| | | | | |
|---|---|---|---|---|
| 2,759,477 | A | * | 8/1956 | Mains .............................. 604/343 |
| 3,123,074 | A | * | 3/1964 | Turner ............................. 604/332 |
| 3,253,594 | A | * | 5/1966 | Matthews et al. .......... 604/103.03 |
| 3,902,496 | A | * | 9/1975 | Eakin ............................... 604/334 |
| 4,085,752 | A | * | 4/1978 | Canale ............................. 604/370 |
| 4,178,915 | A | * | 12/1979 | Szinicz et al. .................... 600/31 |
| 4,319,571 | A | * | 3/1982 | Winchell ......................... 604/342 |
| 4,406,659 | A | * | 9/1983 | Broida ............................. 604/339 |
| 4,419,100 | A | | 12/1983 | Alexander |
| 4,468,227 | A | * | 8/1984 | Jensen ............................. 604/327 |
| 4,586,927 | A | * | 5/1986 | Jensen ............................. 604/342 |
| 4,596,566 | A | * | 6/1986 | Kay ................................. 604/343 |
| 4,778,446 | A | * | 10/1988 | Jensen ............................... 604/27 |
| 4,786,283 | A | * | 11/1988 | Andersson ...................... 604/328 |
| 4,800,900 | A | * | 1/1989 | French ............................. 128/885 |
| 4,850,985 | A | * | 7/1989 | Edwards et al. ............... 604/339 |
| 4,865,594 | A | * | 9/1989 | Thomas .......................... 604/332 |
| 4,923,446 | A | * | 5/1990 | Page et al. ....................... 604/198 |
| 5,144,708 | A | | 9/1992 | Pekar |
| 5,203,806 | A | * | 4/1993 | Broida ............................. 604/338 |
| 5,626,569 | A | * | 5/1997 | Holtermann et al. .......... 604/333 |
| 5,643,241 | A | | 7/1997 | Ahr et al. |
| 5,667,502 | A | * | 9/1997 | Holtermann .................... 604/342 |
| 5,672,163 | A | * | 9/1997 | Ferreira et al. ................. 604/333 |
| 5,688,236 | A | * | 11/1997 | Gragg ............................... 604/23 |
| 6,093,160 | A | | 7/2000 | Augustine et al. |
| 6,110,197 | A | | 8/2000 | Augustine et al. |
| 6,458,109 | B1 | | 10/2002 | Henley et al. |
| 6,659,988 | B1 | * | 12/2003 | Steer et al. ...................... 604/333 |
| 6,689,111 | B2 | * | 2/2004 | Mulhauser et al. ............ 604/332 |
| 6,765,122 | B1 | * | 7/2004 | Stout ................................. 602/41 |
| 7,087,041 | B2 | * | 8/2006 | von Dyck et al. .............. 604/332 |
| 2007/0027434 | A1 | * | 2/2007 | Pedersen et al. ............... 604/333 |

FOREIGN PATENT DOCUMENTS

| | | | |
|---|---|---|---|
| EP | 0 098 718 | A1 | 1/1984 |
| EP | 0 248 657 | A2 | 9/1987 |
| EP | 0 355 186 | A1 | 2/1990 |
| GB | 1 587 604 | | 4/1981 |
| JP | 10503668 | | 4/1998 |
| WO | WO 92/18074 | * | 10/1992 |
| WO | WO2004/015657 | A2 * | 12/2004 |
| WO | WO 2004/105657 | A2 | 12/2004 |

OTHER PUBLICATIONS

Translation of DE 3637355 A1, two pages total.*

* cited by examiner

APPLIANCE FOR IRRIGATION AND/OR DRAINAGE

This is a national stage of PCT/DK06/000274 filed May 19, 2006 and published in English.

BACKGROUND OF THE INVENTION

1. Field of the Invention

The invention relates to appliances for ostomy, fistula, wound or drain site treatment. The invention further relates to means for facilitating the use of such collecting devices.

2. Description of the Related Art

In the treatment of ostomy, fistulae and wounds appliances comprising a collecting bag may be used. Preferably the appliance has an access opening for inspecting, cleaning and/or treating the skin site. The appliance may comprise a body side member in the form of an adhesive wafer secured to the skin and with an opening for receiving the stoma, fistulae or wound. To the wafer is the collecting bag attached, optionally with means for irrigation and/or drainage, such as inlets and outlets. Furthermore, the bag may be provided with an access opening in the form of a window, which can be closed with a lid. When it is time for cleaning or rinsing the skin site comprising the stoma, wound or fistulae, the lid is removed, and the site may be inspected or treated. A problem relating to such appliances is to prevent body liquids and excreta from exiting out of the collecting bag, when the lid is removed and during treatment of the site.

As the appliance is generally flat and substantially two-dimensional, problems may arise especially when the device is applied to larger skins sites and to curved or protruding body parts. It may be difficult to prevent leakage of liquids from the bag in such situations. Attempts to solve the problem have been made:

U.S. Pat. No. 4,778,446 discloses a device for irrigation and/or drainage, which comprises a rigid or semi-rigid cylindrical hollow open-ended collar that is mounted on an adhesive wafer. A lid may be mounted on the non-skin-facing end of the collar. In order to avoid the lid to contact the wound site, the collar has to be rather stiff/rigid. Flexibility is needed between the collar and the adhesive wafer in order to follow the contours of the body and movements of the skin and this is achieved by having an accordion-like portion between the collar and the wafer. The device is voluminous and may be uncomfortable due to stiffness and the accordion-like portion has to be lifted and held by hand in order to stay in place. Closing the collar and inflating the whole device may also lift the accordion-like portion. However, it will then be impossible to access the wound site directly, as the device collapses if opened and pressure drops. Access to the wound will then only be indirectly by the use of tubes or the like.

In U.S. Pat. No. 4,419,100 is disclosed an ostomy collecting bag wherein it is possible to provide a distance between the adhesive wafer and the access opening due to the presence of a wall of flexible material between the wafer and the access opening. A certain mobility of the two parts relative to each other is thus provided, and by inserting one or more fingers of the user between the wafer and the access opening, the wall is raised to an erect position, thus creating the desired distance between the two parts. However, the raised position is only maintained by the presence of the users hand, as soon as he lets go the construction will collapse and return to its initial generally flat condition.

U.S. Pat. Nos. 6,093,160 and 6,110,197 discloses a wound treatment device comprising an adhesive wafer for adhering to the skin and a support member, preferably in the form of a ring-shaped foam cushion. The support member is attached to the adhesive wafer on one surface, and on the opposite surface is provided an access opening with means for attaching a lid. The support member provides a constant distance between the lid and the wound site, thus protecting the wound and facilitating cleaning of the wound and controlling the liquid. The support member provides a constantly raised portion and is not suitable for larger wounds and/or application on curved or protruding body parts, as the construction is rather stiff.

U.S. Pat. No. 3,902,496 discloses a surgical drainage appliance, prepared from thin plastic material and comprises gas or foam filled plastic cushions located on either side of inlet for the stoma so as to protect it in use. The cushions are mounted inside the bag and are permanently inflated/foam filled, thus the amount of gas/foam cannot be adjusted during use. The bag is closed without a window, and the cushions are located right next to the stoma, for protecting this.

In U.S. Pat. No. 5,667,502 is disclosed a collecting bag for an artificial anus, said bag comprises an inflatable cushion that may be inflated to a desired level in order to protect the artificial anus. The cushion is preferably in the form of a half-circle, mounted over and around a part of the stoma. The cushion is mounted inside the bag.

None of the above-mentioned references solves the problem of providing an appliance for irrigation and/or drainage comprising a barrier against leakage that can be erected and maintain erected without the help of a person, and that can be collapsed when desired.

Thus there is still a need for providing an appliance for cleansing of a skin site, said appliance being capable of providing a stable erect wall for controlling the fluid inside the appliance, and further with flexibility offering the access opening and the adhesive wafer to operate substantially independent of each others, facilitating the application of the lid.

SUMMARY OF THE INVENTION

It is an object of the present invention to provide a device for wound irrigation and drainage where the site may be attended without risk of leakage.

It is a further object of the present invention to provide an appliance for cleansing a skin site where a raised wall may be provided when the site is accessed.

It is further an object of the present invention to provide an appliance wherein the stress in the appliance is reduced by rendering it possible for the access opening of the device and the body side member to operate more independent of each other's.

Furthermore, it is an object of the present invention to provide an appliance wherein the coupling means of the access opening may be substantially planar during the application of a lid.

Yet another object is to provide means for stabilizing the wall in upright position and at the same time facilitating that the coupling flange is able to move substantially independently of the adhesive wafer.

Still another object of the present invention is to provide an appliance wherein the walls may be raised to a stable, substantially upright position and collapsed to a substantially flat position as desired.

BRIEF DESCRIPTION OF THE DRAWINGS

The invention is disclosed more in detail with reference to the drawings in which.

DETAILED DESCRIPTION OF THE PRESENT INVENTION

The invention relates to an appliance for irrigation and/or drainage, which appliance comprising a body side member comprising an adhesive wafer for securing the appliance to the patient's skin, said wafer can be provided with an aperture for receiving a stoma, surrounding a wound, a fistula or a drainage site, a wall of flexible material, the wall comprising a rear wall and a front wall, the rear wall being attached to the wafer and having an opening suitable for surrounding the surface area of the skin to be cleansed and a front wall being provided with a coupling flange adapted for removable coupling and sealing to a matching coupling means, the wall and the body side member defining a reservoir 30 (FIG. 2), a sealed chamber, being separate from reservoir, said chamber when inflated, provides a distance between the adhesive wafer and the coupling flange.

When the sealed chamber is not inflated, the wall is collapsed and the appliance is substantially flat and two-dimensional, and does not take up unnecessary space during storage and when applied to a body part. When the wound or fistulae needs inspection, cleaning or other treatment, the sealed chamber may be inflated, thus raising the walls of the appliance and creating a distance between the flange and the wafer. The erected wall and the wafer may thus define a reservoir. The raised walls decrease the risk of splashing and leakage during the rinsing process. When cleansing/inspection is finished, a lid may be applied and the chamber can be deflated again returning the appliance to its original flat configuration. Alternatively, the chamber may stay constantly inflated, thus creating a buffer zone around the fistulae or wound.

The sealed chamber may be a part of the wall or connected to the wall and constitutes a delimited volume being air and liquid tight separated from the reservoir. The sealed chamber may be contained in the reservoir, i.e. being in the form of a balloon along the inside or outside wall of the reservoir, or be a part of the wall, but the chamber is designed in such a way that it is possible to directly access the wound or fistulae through the opening of the appliance.

Figure 2:
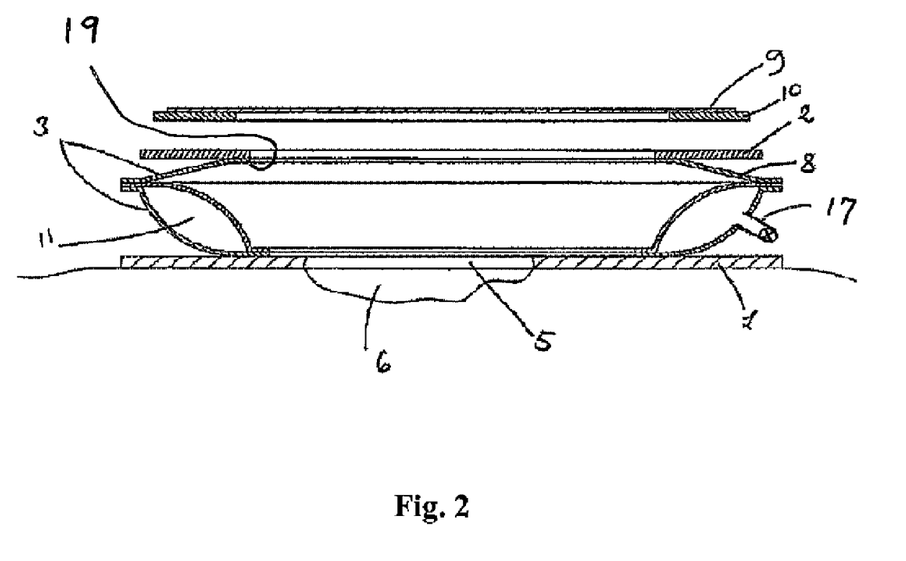
FIG. 2 shows the same embodiment in cross-section.
Figure 8:
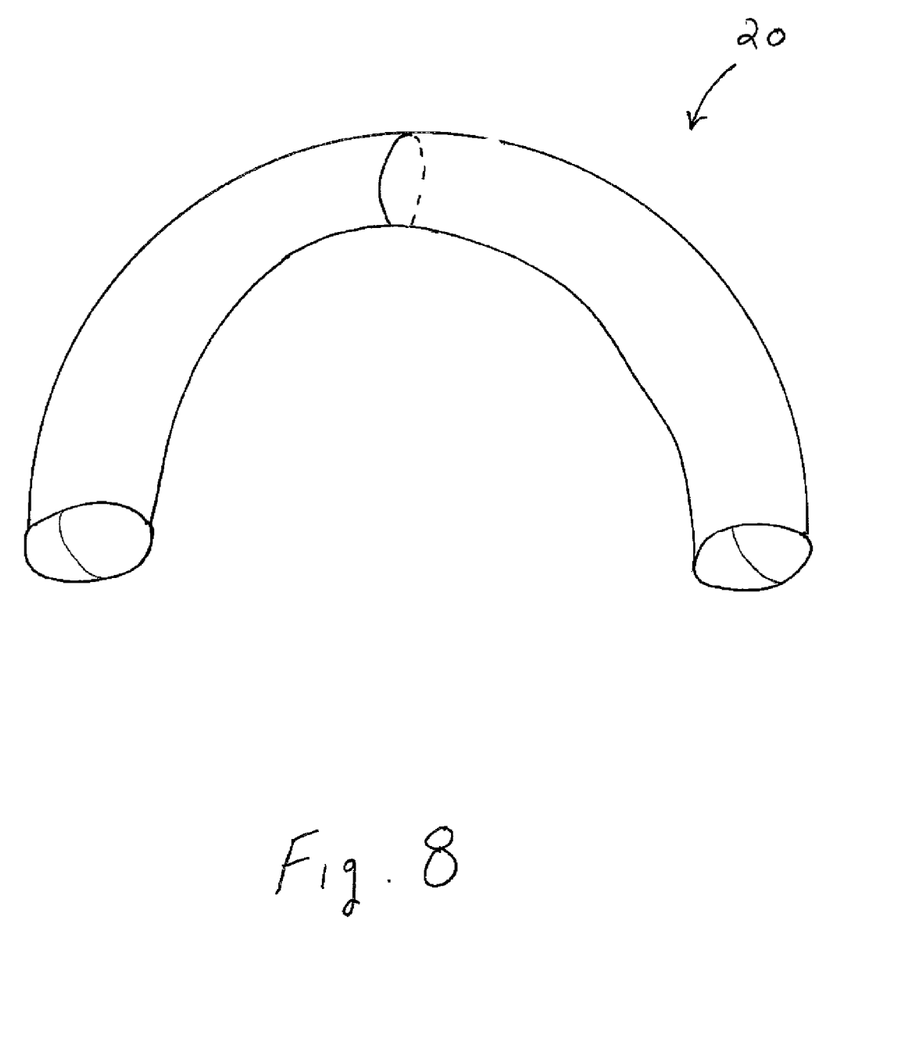
FIG. 8 shows an embodiment of an open ring sealed chamber in a horseshoe configuration.

It is preferred that the sealed chamber is following a major part of the circumference of the wall of the appliance, e.g. being in the form of a circular or oval ring or an open ring, such as open ring 20 illustrated as a horseshoe-configuration in FIG. 8. The chamber may be placed inside the walls, in the reservoir, or the chamber may be placed on the outside of the wall. It may be preferred to have the chamber on the outside of the walls as it may take up space in the reservoir and may create undesired corners that may accumulate contaminated material. The reservoir is accessible through the opening 19 (as illustrated in FIG. 2) when the chamber is inflated. Prior art shows appliances wherein the reservoir itself is inflated. This solution suffers from the drawback that the reservoir can only be attended through a closed system, as the reservoir otherwise will collapse if the reservoir is opened. In the appliance of the present invention to sealed chamber is separate from the reservoir and can thus be inflated independently of the reservoir and the walls of the appliance can thus be erected without inflating the reservoir.

Any suitable fluid such as a gas or a liquid may inflate the chamber. In one embodiment of the invention the fluid is a gel. Preferably the chamber is inflated by air. The sealed chamber may be prepared from any suitable material being flexible and able to detain gas and/or liquid. The chamber may be in the form of a tube; prepared from a tube-like structure or it may be in the form of one or more sheets being sealed together to provide an inflatable chamber. The chosen material for the chamber should be flexible but yet rigid enough to support and keep the two elements in a preferred stable distance.

In one embodiment of the invention the sealed chamber constitutes a part of the wall.

The sealed chamber may be an integrated part of the appliance. The chamber may constitute a part of the wall of the appliance of the invention or it may be substantially independent of the wall. The chamber may be attached to the wall by a single point or by sharing a part of the wall. It is preferred that the part of the wall that may constitute a part of the chamber is less than 50% of the wall. The larger part of the wall constituting the chamber, the less independency in the movement of the wall is achieved.

The height of the sealed chamber, when expanded, is preferably smaller than the height of a fully erected wall, in order to provide space for flexibility. Preferably the height is less than 75% more preferred more preferred less than 60% and most preferred less than 50%.

The chamber may be attached to the coupling flange or to the wall next to the coupling flange or the chamber may be attached to the adhesive wafer or the front wall next to the wafer.

The wall of the appliance comprises a rear wall and a front wall. Preferably, the front and the rear wall may be sealed together in such a manner that the two walls are superimposed when the wall I collapsed. However, the front and rear wall may also be prepared as a single sheet, thus folding e.g. like an accordion when collapsed. This embodiment may however be complicated to produce, so the embodiment with two connected sheets may be preferred. The wall may be prepared by folding and welding the sheet in such a way, that it creates a "box form" when it is in use. Folding the film several times, or forming or welding many layers of film together can achieve an accordion design, which can be adjusted to a varying change of position rise.

It is desired that the wall of the appliance may be raised when the skin site is attended, and that the wall is able to stay erected without being actively supported by the user, e.g. held by the hand. The erected wall provides a reservoir over the skin site, securing any liquids around the skin site stays inside the reservoir and thus decreases unhygienic situations from leakage and overflow. The construction is still flexible due to a balloon effect of the sealed chamber and not as rigid as a foam structure.

Rising of the coupling flange is today done by manually erecting e.g. by grabbing the coupling flange with the fingers and elevating, thus erecting the wall of the appliance. Only the design and stiffness of the wall ensures the preferred distance momentarily. The wall is having a tendency to collapse thus bringing the appliance to a substantially flat configuration and may cause body liquid to exit out of the bag, thus creating a hygienic problem. To avoid this problem, more than one person is needed for the care situation, which is inconvenient. A solution to this problem is to have a surrounding protrusion profile in the attached coupling part, which can function as a barrier wall, while the detachable coupling part in the form of a lid or collecting/drainage bag is removed from the access opening.

If an appliance is applied to a curved body part it may be exposed to severe stress from twisting and bending. Furthermore, when the wall is raised, the coupling flange, typically being more rigid than the wall, may also twist if it has to follow the adhesive wafer. Stress may be build up in the appliance leading to detachment from the skin, discomfort for the patient and difficulties when attaching a lid or bag to the coupling flange.

It is preferred that the sealed chamber, when inflated, supports at least one of the walls.

In one embodiment of the invention the sealed chamber, when inflated, supports the rear wall.

In another preferred embodiment of the invention the sealed chamber, when inflated, supports the front wall.

By having the sealed chamber supporting one of the walls of the collecting chamber, it may be possible for the wall of the appliance to be supported in such way that at least one wall can be straightened out and due to some resistance against crumpling up the other wall stays partly straightened out, and hereby rendering it possible level the coupling flange and thus facilitating the connection of the lid to the coupling flange. Thus, the adhesive wafer follows the contours of the body part, while the raised coupling flange may enter a more planar configuration, substantially independent of the configuration of the wafer.

The sealed chamber may be connected to the adhesive wafer or to the wall near or next to the adhesive wafer. In this embodiment of the invention the sealed chamber may erect the rear wall. The front wall may be partly erected by influence of the coupling flange, the flange having a higher rigidity and thus an inherent desire to revert to its initial planar configuration.

In a preferred embodiment of the invention the sealed chamber is connected to the coupling flange or to the front wall near or next to the flange. The sealed chamber erects the front wall when inflated and fully or partly the rear wall. As the sealed chamber is placed right under the coupling flange, it will contribute to the levelling of the flange, while the rear wall may serve as a buffer, absorbing the stress of twisting from the adhesive wafer.

The wall may be provided with an opening 19 as illustrated in FIG. 2, preferably in the form of an inlet and/or outlet opening for entering fluids in or out of the reservoir and for accessing the skin site.

The sealed chamber may be inflated and deflated during use of the appliance. Thus, the chamber may be inflated when the skin site is attended, and deflated when the appliance is closed with a lid or collection bag. However, the chamber may also be used as permanently inflated if that may be desired.

The adhesive wafer of the appliance of the present invention may be made from any appropriate skin friendly material known per se for the purpose and may also comprise a top film known per se. The skin-friendly adhesive may be any skin-friendly adhesive known per se, e.g. an adhesive comprising hydrocolloids or other moisture absorbing constituents for prolonging the time of use. The coupling flange for attaching a collection bag or a lid may be a system known per se comprising matching coupling rings or matching flanges and adhesive surfaces.

The adhesive wafer may be provided with an aperture corresponding to the contour of the stoma, fistulae or wound. The wafer may be provided with an aperture being tailor-fit to the patient, or a drawing of the desired contours of the aperture may be printed on the wafer for cutting before application. In one embodiment of the invention the wafer is provided with a standard cut aperture. Typically, the appliance may be delivered without an aperture leaving opportunity for the health care personnel to provide a custom made aperture in the wafer.

The invention also relates to an sealed chamber for use with an appliance for irrigation and/or drainage, which appliance comprising a body side member comprising an adhesive wafer for securing the appliance to the patient's skin, said wafer or pad can be adapted for receiving a stoma, surrounding a wound, a fistula or a drainage site, a wall of flexible material, the wall comprising a rear wall being attached to the wafer and having an opening suitable for surrounding the surface area of the skin to be cleansed and a front wall being provided with a coupling flange defining an aperture/window of the wall, the wall and the body side member defining a reservoir, and wherein the sealed chamber, being separate from the reservoir, can be inflated by filling with a fluid, said chamber, when inflated, provides a distance between the adhesive wafer and the coupling flange.

The sealed chamber may be an integrated part of the appliance or it may be a separate unit. In one embodiment of the invention the chamber is detachable from the appliance.

The sealed chamber may extend along the outer periphery of the wall. The chamber may be in the form of a closed ring, but is preferably and open ring. In one embodiment of the invention the open ring is provided with means for connecting the end portions, rendering it possible to attach the two end portions of the ring to each other's to achieve a closed ring. The connecting means may be any suitable means known per se, such as adhesive, Velcro or a mechanical lock. In another embodiment of the invention the chamber extend only along a part of the wall, e.g. having the shape of a horseshoe.

The sealed chamber is provided with a valve 17 as illustrated in FIG. 2 for filling or emptying the fluid. The chamber may be inflated with any suitable liquid or gas, especially air. The valve may be any kind of valve suitable for the purpose. The kind of valve used for inflating the sealed chamber may for example be of the type known from inflatable mattresses or swimming rings, where it is possible to connect an inflation device, such as a pump, inflate the substance and removed the device, without the substance escaping out of the valve. By pushing the valve's sides together, it is possible to empty the inflated substances through the same connection. To prevent this from occurring accidentally, a detachable plug can be attached.

The inflation device may also be an integrated part of the appliance, for example a valve as disclosed in U.S. Pat. No. 5,144,708.

The coupling flange may be equipped with a lid or a collection or drainage bag.

The lid or bag is connected to the coupling flange be known means such as e.g. adhesive or a mechanical coupling.

In some situations the treatment of the skin site include the use of drainage tubes, to transport body liquids directly from the patient or from the inside of the appliance. This is commonly done by accessing through the walls of the appliance or through the access opening or lid. The drainage tubes are very easily displaced or misaligned, caused by movement of the patient, do to the unstable fixation means through and to the appliances surfaces.

The sealed chamber may be provided with incisions or a non-inflated portion so as to render it possible for body liquids can escape through, into a collecting bag. This space can be a simple opening, but to prevent body liquids from exiting back into the wound, a "non return valve" may be achieved as an extra security.

An example of such a "non return valve" is described further in patent EP 248 657 B1.

To be able to improve patient's needs and comfort regarding a bandage for wound treatment, that is comfortable to wear, flexible and discrete under clothes, it is essential that the appliance have as low overall profile as possible. Such appliances are commonly attached to the patient's skin, with an adhesive wafer, which often is provided with a collecting bag on the second surface. The adhesive wafer is cut to fit the specific wound size, so the remaining wafer covers and protects the surrounding skin against the body liquids and excreta from the wound. The wear time of the appliances, depend on the hygienic situation or if a leak occurs, causing the appliance to be changed. A premature changing situation can cause the protected skin to be "striped" and also be painful for the patient and should be avoided if possible. To improve the wear time and use of the appliance, an access opening can be integrated in the design, in the form of a coupling flange, placed above the wafer, where through it is possible to treat and clean the wound, and thereby delaying or prevent leaks from occurring, without removing the surrounding appliance. The coupling means used, may be similar as the ones known from ostomy bags two-pieces attachments. Thus an appliance according to the present invention provides a substantially flat and discrete bandage that may turn into a three-dimensional configuration when the wound needs attention.

The rising of the flange may be adjusted to the desired extent, providing a preferable space between the coupling flange and the adhesive wafer, causing liquids and solid excreta to handled safely and be washed easily out.

Furthermore the wound or fistulae or stoma may be protected against pressure from the lid, clothes, bed quilts, or similar by the inflated chamber.

When the coupling flange is raised, it creates a space under the coupling flange, enabling the nurse to put fingers underneath, to exert a counter pressure needed to insure a proper sealing of the lid.

The ability to stabilize the appliance is an advantage when a drain is fixated through or to the bandage, making the drain and fixation means less vulnerable to movement of the patient.

In one embodiment, a safety feature can be achieved if the non-return valve is blocked or the collecting bags gathering is accumulated, the sealed chamber of the bag may be designed in such a way, that if inflated with a fluid with a density below the body liquids, it may automatically float on top of the body liquid if this amount should increase during use.

The appliance of the present invention may comprise more than one inflatable chamber. The presence of two or more chambers that may be inflated and regulated individually may facilitate application on curved body parts.

Furthermore, it should be obvious that the rising of the coupling flange may be further controlled by the amount of fluid in the sealed chamber.

If it is less important for the user that the appliance of the present invention may be inflated and deflated during use, the sealed chamber may be substituted with other kind of rising means than an inflatable member. The rising means may be in the form of a pad or tube or brace prepared from a flexible material. Examples of such material may be foam, natural or synthetic rubber or silicones. The rising means may be an integrated part of appliance or it may be a separate unit that may be inserted under the coupling flange when needed, and removed again after use. In one embodiment of the invention the rising means is a relatively stiff brace, e.g. prepared from a polymer material such as plastic.

DESCRIPTION OF THE PREFERRED EMBODIMENTS

The invention is now explained more in detail with reference to the drawings showing preferred embodiments of the invention.

Figure 1:
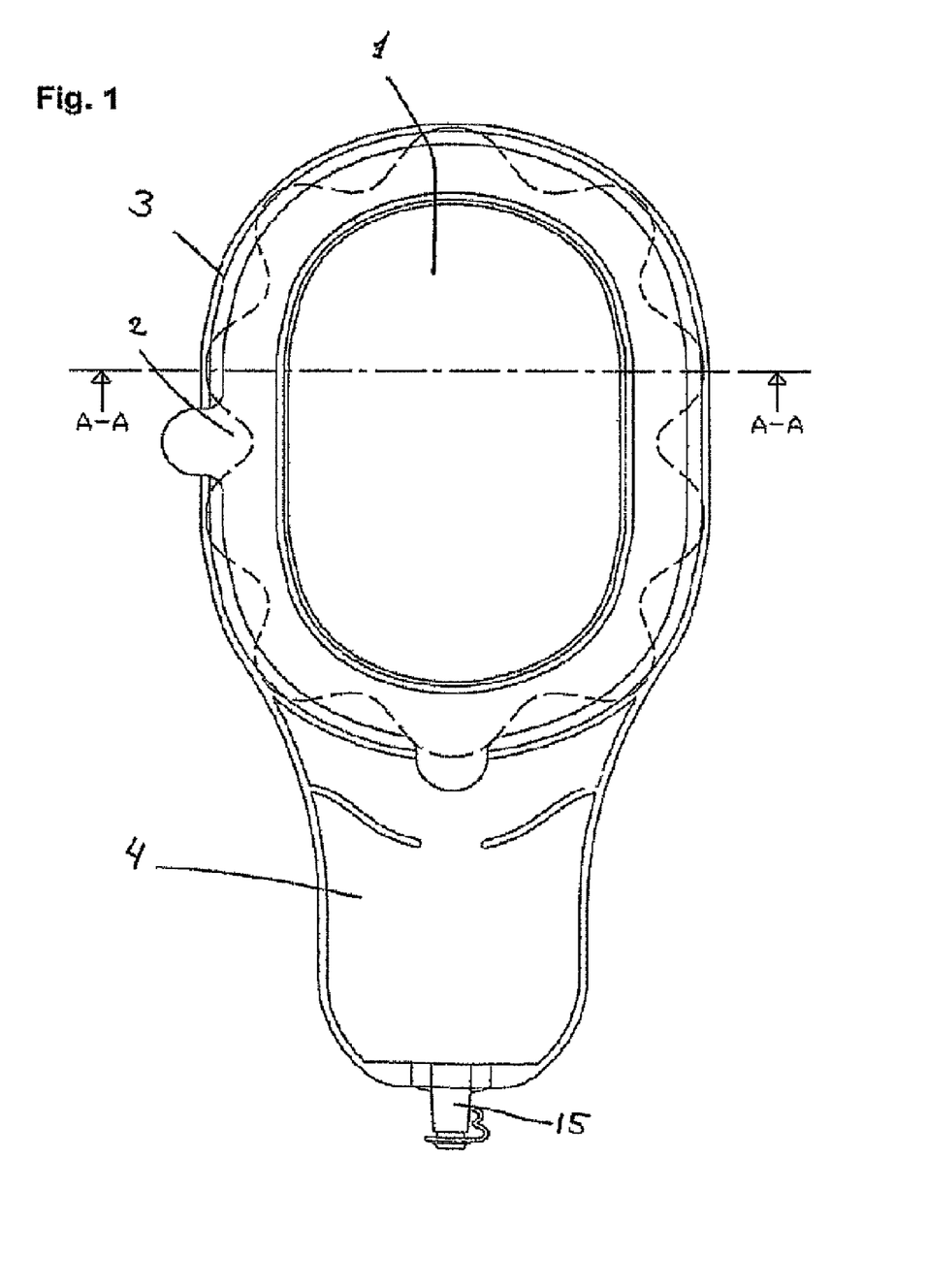
FIG. 1 shows an embodiment of the invention seen from above.

FIG. 1 shows embodiment of the invention seen from above. The appliance comprises an adhesive wafer (1), here shown with a wave-shaped edge portion, and a coupling flange (2) that may be provided with a lid. The wall (3) of the appliance extends into a collecting bag (4) with a valve 15 provided for removal of effluent.

FIG. 2 shows a cross-section of the embodiment along the A-A line of FIG. 1. The appliance comprises and adhesive wafer (1) for securing the appliance to the body part, the wafer (1) is provided with an aperture (5) for receiving the wound, stoma or fistulae (6). A wall (3) is extending away from the wafer (1); the wall comprises a rear wall (7) connected to the wafer (1) and a front wall (8) being provided with a coupling flange (2) adapted for coupling and sealing with corresponding coupling means. A lid (9) with corresponding coupling means (10) is mounted on the coupling flange (2). The rear wall (7) comprises a sealed chamber (11). The chamber (11) is shown in inflated position. When the chamber (11) is deflated, the wall (3) may collapse and the appliance will return into a substantially flat configuration.

Figure 3:
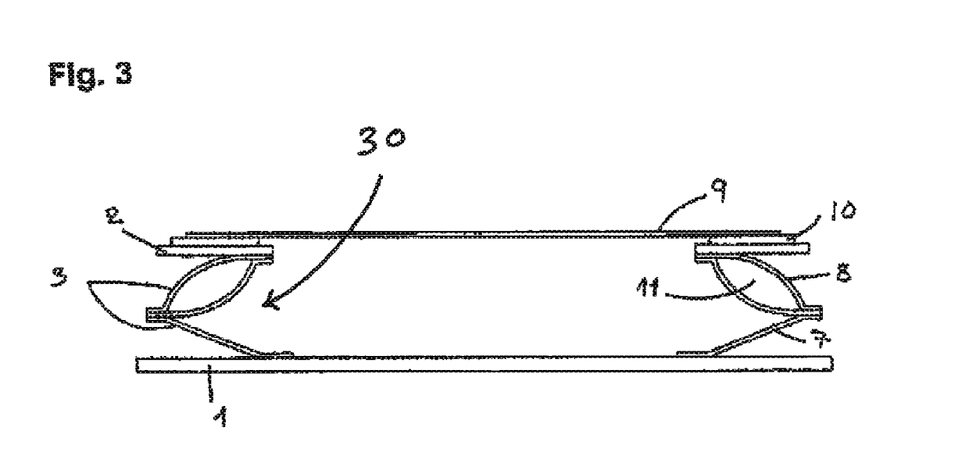
FIG. 3 shows another embodiment in cross-section.

In FIG. 3 is shown an embodiment of the invention wherein the sealed chamber (11) is an integrated part of the front wall (8).

The position of the sealed chamber is important with regard to the behavior of the appliance. Applied onto flat or slightly curved body parts, the position of the chamber is not as important as if the appliance is applied to curved and protruding body part where it may be subjected to severe stress from twisting and bending.

Figure 4A:
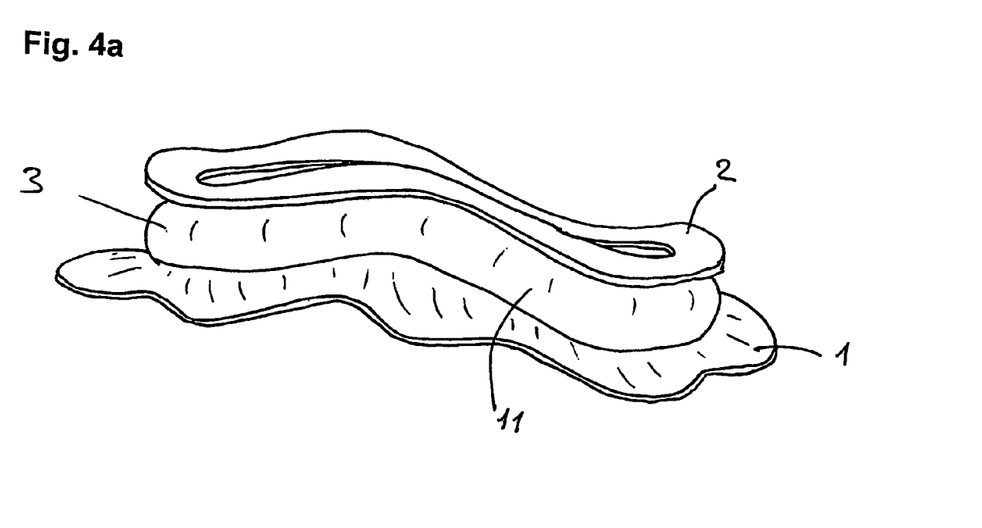
FIGS. 4a and 4b show an embodiment applied to a curved body part.
Figure 4B:
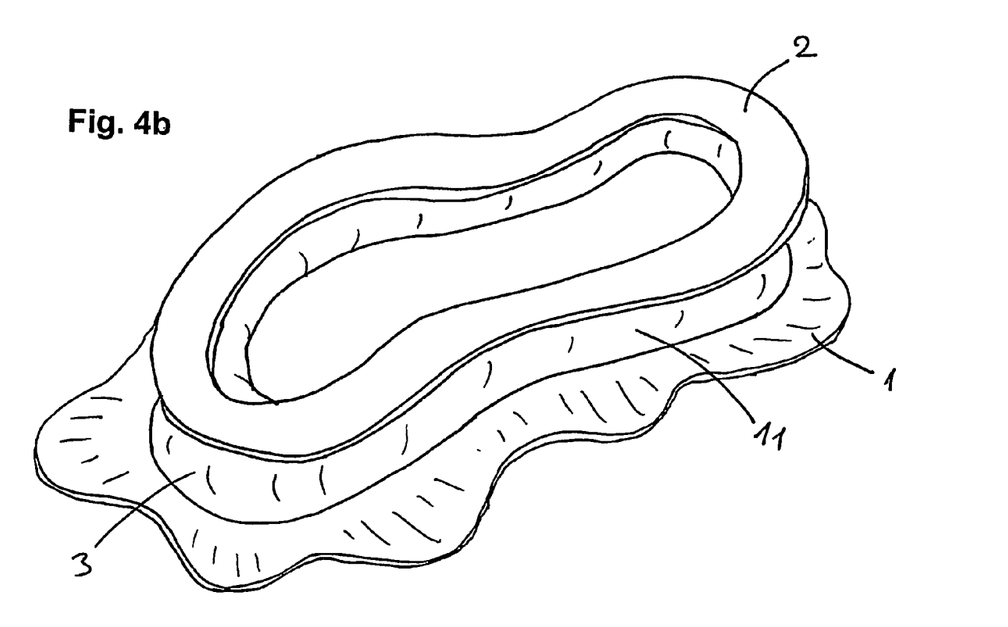

FIGS. 4a and 4b shows an appliance where the sealed chamber (11) constitutes the wall (3) of the application, applied to a curved body part. As can be seen from FIGS. 4a and 4b, the wall (3) is fully erected by the inflation of the chamber (11), and the configuration of the coupling flange (2) substantially follows the configuration of the adhesive wafer (1), hence the twisting forces are linked. The situation demands a strong adhesive of the wafer (1) in order to avoid the twisting forces may bring the adhesive to detach from the skin. Furthermore, the coupling flange (2) is also curved and twisted and it may be difficult to apply a lid to the flange (2) in a correct and safe manner. The forces of the sealed chamber (11) is transferred directly to the coupling flange (2), making it more difficult to apply the lid, especially if the lid is in the form of a thin and flexible foam flange provided with a transparent film.

Figure 5A:
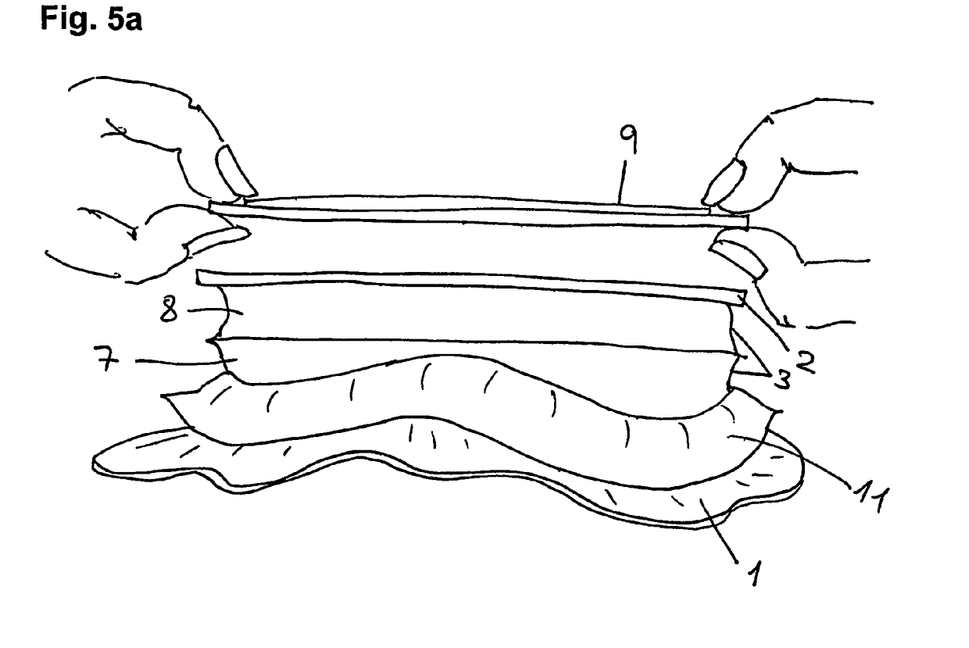
FIGS. 5a and 5b show another embodiment applied to a curved body part.
Figure 5B:
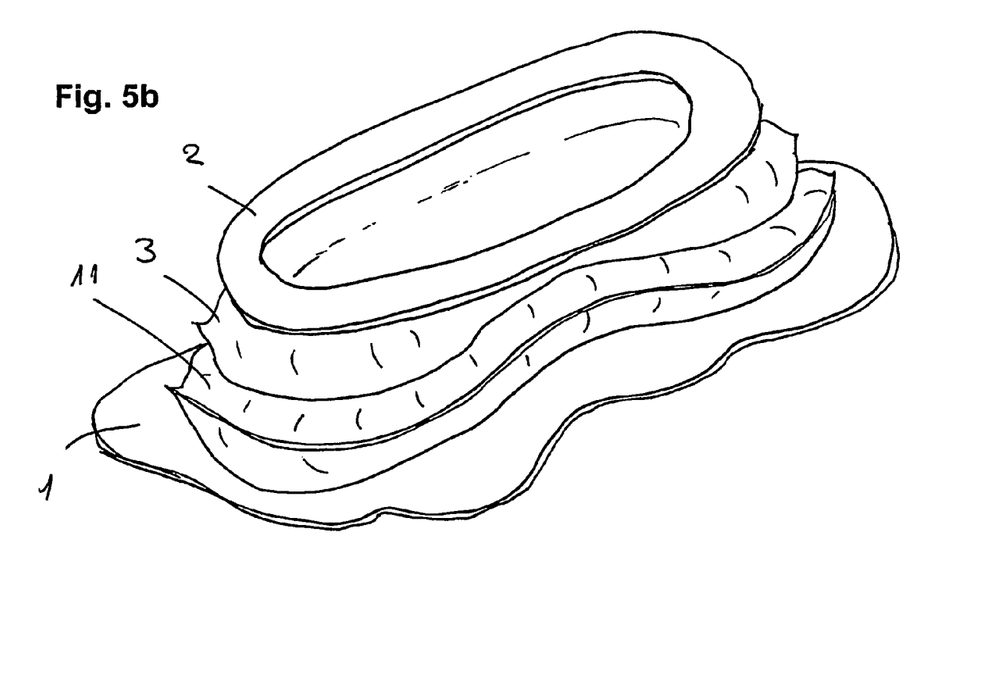

FIGS. 5a and 5b disclose an embodiment of the invention wherein the chamber (11) is placed outside the wall (3) and right next to the adhesive wafer (1). The chamber (11) may share a part of the rear wall (7) or it may be substantially independent of said wall (7). As can be seen from FIGS. 5a and 5b, the wafer (1) and the coupling flange (2) move more independently of each other's, even though the wafer (1) is curved and twisted, the coupling flange (2) continues to be substantially planar and it may be easy to apply the lid (9). The flange (2) may be stiffened by the presence of the inflated chamber (11) and thus more planar in configuration. The chamber (11) supports the rear wall (7) to an upright position, while the front wall (8) may accommodate the twisting forces by straightening out in some portions and collapsing in other portions.

Figure 6A:
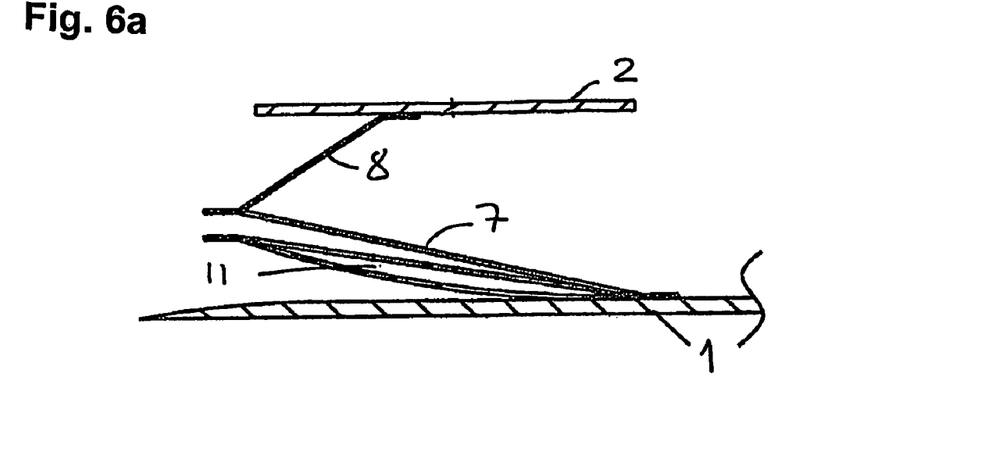
FIGS. 6a, 6b and 6c show three different embodiments

Hence, for use on curved body parts it may be an advantage if the chamber is placed in connection with the coupling flange or the front wall as the coupling flange may operate more freely in this way and less stress is induced in the adhesive wafer. Attaching the chamber in direct contact with the adhesive wafer may bring the twisting and bending forces to enter the adhesive wafer from the chamber. By having the coupling part straightened out before mounting a lid, one reduces the risk of having undesirable channels made in the thin and flexible foam In one embodiment of the invention the chamber (11) may be placed next to, but not being a part of, the wall (3), see FIG. 6a. When the chamber (11) is inflated it will force the rear wall (7) to rise, while the front wall (8) may absorb the twisting and bending forces by rising more or less around the circumference of the coupling flange.

Figure 6B:
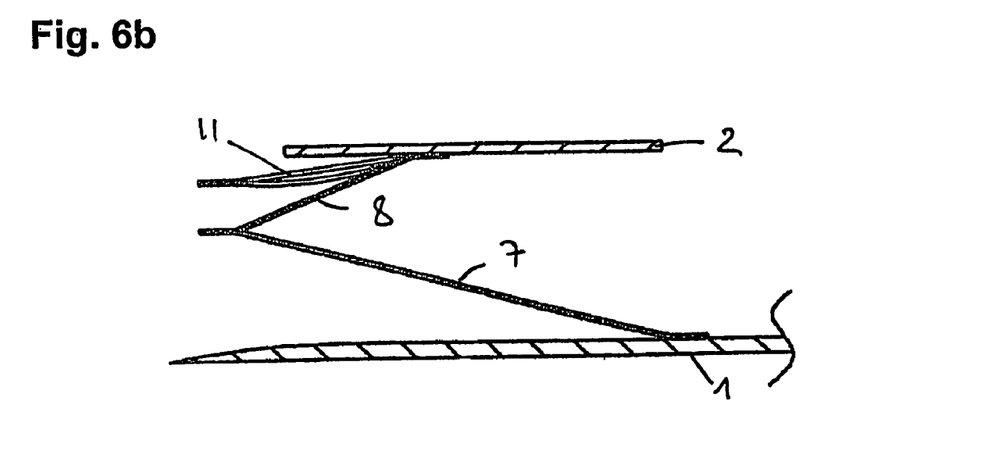

In FIG. 6b is shown a preferred embodiment of the invention wherein the chamber is placed right under the coupling flange, attached to the front wall and the flange, but preferably not being a part thereof.

Figure 6C:
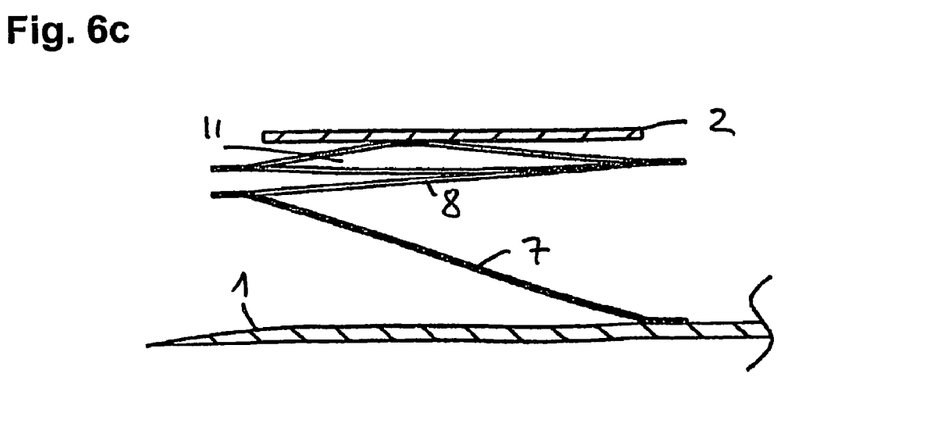

In FIG. 6c the chamber is a part of the front wall. The attachment point of the front wall and the chamber to the coupling flange may be anywhere over the skin-facing surface of the coupling flange, but it is preferred that it is at the central portion or towards the periphery of the flange, as this may provide the flange with maximum stability.

Figure 7:
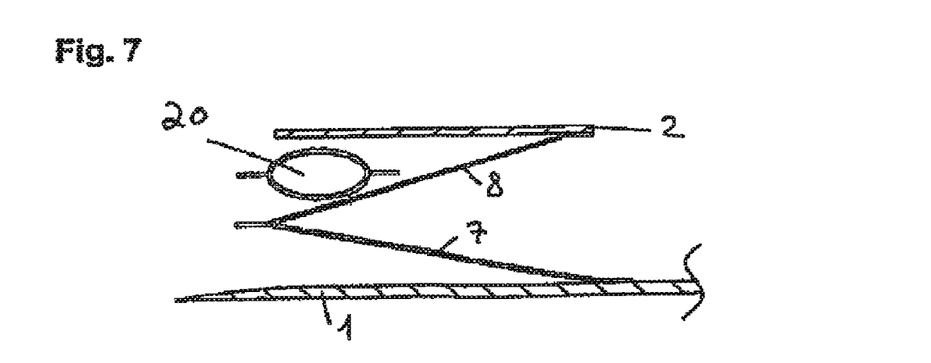
FIG. 7 shows an embodiment of the invention wherein the chamber is separate.

In one embodiment of the invention the chamber is in the form of a separate element, e.g. a tube-shaped balloon 20 such as the tube-shaped balloon illustrated in FIG. 8 and referred to above as the open ring 20 horseshoe-configuration, which may be placed along the outside of the wall to erect the wall, and be removed when not in use, see FIG. 7. The chamber may be attached to the appliance by detachable means (not shown).

Instead of a balloon, the chamber may comprise a foam. Such chamber may not be inflated and deflated as such, however, the foam may be delivered in a compressed state and after decompression expand to full size. If decompressed foam is used, it may be e.g. compressed by vacuum-pack or squeezed in a removable wrapping.

The invention claimed is:
1. An appliance for irrigation and/or drainage comprising:
   a) a body side member including an adhesive wafer for securing the appliance to a patient's skin, said adhesive wafer defining an aperture for receiving a stoma or a drainage site;
   b) a front wall and a rear wall of flexible material, the rear wall being attached to the wafer and having an opening providing access to a surface of skin to be cleansed, and the front wall attached to a coupling flange adapted for removable coupling with a matching coupling member, the walls and the body side member defining a flexible reservoir that extends between the wafer and the coupling flange; and
   c) a sealed chamber separate from the adhesive wafer that defines the aperture, the sealed chamber inflatable to provide a distance of separation between the adhesive wafer and the coupling flange.

2. The appliance according to claim 1 wherein the sealed chamber, when inflated, supports at least one of the walls.

3. The appliance according to claim 1 wherein the sealed chamber, when inflated, supports the rear wall.

4. The appliance according to claim 1 wherein the sealed chamber, when inflated, supports the front wall.

5. The appliance according to claim 1 wherein the sealed chamber is provided with a valve.

6. The appliance according to claim 1 wherein the sealed chamber constitutes a part of at least one of the front wall or the rear wall.

7. The appliance according to claim 1 wherein the sealed chamber is next to the coupling flange.

8. The appliance according to claim 1 wherein the sealed chamber is next to the adhesive wafer.

9. The appliance according to claim 1 wherein at least one of the front wall or the rear wall is provided with an opening.

10. The appliance according to claim 1 wherein at least one of the front wall or the rear wall is provided with an inlet/outlet opening.

11. The appliance according to claim 1 wherein the sealed chamber can be inflated and deflated during use of the appliance.

12. The appliance according to claim 1 wherein the wafer is provided with an aperture corresponding to a contour of the stoma.

13. A sealed chamber for use with an appliance for irrigation and/or drainage, the appliance including a body side member having an adhesive wafer for securing the appliance to a patient's skin, said wafer being adaptable to receive a stoma or a drainage site, a first wall attached to the wafer and having an opening suitable for surrounding the surface area of the skin to be cleansed and a second wall provided with a coupling flange, the walls and the body side member defining a flexible reservoir that extends between the wafer and the coupling flange, said sealed chamber separate from the adhesive wafer and configured to be inflated with a fluid, said sealed chamber, when inflated, providing a distance of separation between the adhesive wafer and the coupling flange.

14. The sealed chamber according to claim 13 wherein the chamber is an integrated part of the appliance.

15. The sealed chamber according to claim 13 wherein the chamber is a separate unit relative to the appliance.

16. The sealed chamber according to claim 13 wherein the chamber substantially encircles the walls of the appliance.

17. The sealed chamber according to claim 13 wherein the chamber is provided with a valve.

18. The sealed chamber according to claim 13 wherein the chamber is shaped as an open ring having open ends.

* * * * *